United States Patent [19]

Bombardelli et al.

[11] Patent Number: 5,250,722
[45] Date of Patent: Oct. 5, 1993

[54] TAXANE DERIVATIVES, THEIR PREPARATION AND USE IN ONCOLOGY

[75] Inventors: Ezio Bombardelli; Bruno Gabetta, both of Milan, Italy

[73] Assignee: Indena S.p.A., Milan, Italy

[21] Appl. No.: 881,047

[22] Filed: May 11, 1992

[51] Int. Cl.$^5$ ............................................. C07C 69/76
[52] U.S. Cl. ........................................ 560/104; 560/27; 560/28
[58] Field of Search ................. 560/104, 27, 28; 514/533, 534

[56] References Cited

PUBLICATIONS

CA 112(25): 232506d 1989.
CA 110(25): 225001r 1989.
CA 116(15): 143382a 1991.
CA 116(7): 50886c 1991.
CA 116(5): 41793t 1992.
CA 91(19): 157944n 1979.
CA 95(7): 58056a 1981.
CA 115(13): 13677j 1991.

Primary Examiner—Paul J. Killos
Attorney, Agent, or Firm—Mathews, Woodbridge & Collins

[57] ABSTRACT

The preparation of new 3,11-cyclotaxanes having the general formula 1. Cyclotaxane 1a (1, R'=R''=H) may be isolated from plants of the genus Taxus. New cyclotaxanes 1 have antiblastic activity.

10 Claims, No Drawings

TAXANE DERIVATIVES, THEIR PREPARATION AND USE IN ONCOLOGY

The present invention pertains to new 3,11-cyclotaxane derivatives, to their preparation and to their use in oncology.

The new compounds have the general formula 1

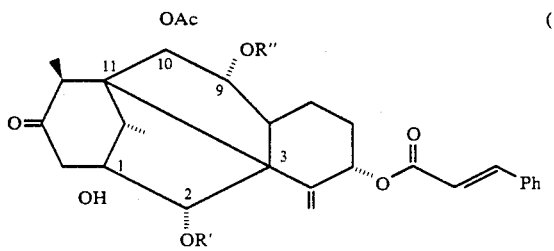

wherein each of R' and R", independently of the other, is hydrogen, alkanoyl of 2 to 7 carbon atoms, —CO—CHOHCH($C_6H_5$) NHCOC$_6$H$_5$, or —CO-CHOHCH($C_6H_5$)NHCOOC(CH$_3$)$_3$.

The cyclotaxane 1a (1, R'=R"=H) is a new natural compound obtainable substantially free of other taxicins and taxines by extraction of needles of plants of the Taxus genus, e.g. Taxus baccata L.. Its structure was determined by spectroscopical analysis, namely 1H-NMR and 13C-NMR. The structure 5-O-cinnamoyl10-acetyl-phototaxicine was in fact assigned to 1a. The new cyclotaxane 1a can be isolated by extraction at room temperature of the vegetable materials with alcohols, e.g. methanol or ethanol, or aliphatic ketones, e.g. acetone, or with their mixtures with water. The extracts, after concentration under vacuum till the removal of the organic solvent, are filtered from any precipitated insoluble material and treated with a water immiscible aprotic solvent such as methylene chloride, chloroform or ethylacetate. The organic extract containing 1a is evaporated to dryness and purified by column chromatography, using silica gel as stationary phase and solvent mixtures such as nhexane, ethyl acetate, methylene chloride/methanol, or acetone/toluene as eluents. The fractions containing 1a are concentrated to dryness under vacuum and the residue crystallized from ethyl acetate.

The compound 1a also can be obtained starting from the natural compound 2, which also can be isolated from Taxus plants, by irradiation at 240 nm in ethanol solution with a mercury lamp.

Under these conditions, the formation of the bond between the carbon atoms in the position 3 and 11 and the migration of the proton from the position 3 to the position 12 take place.

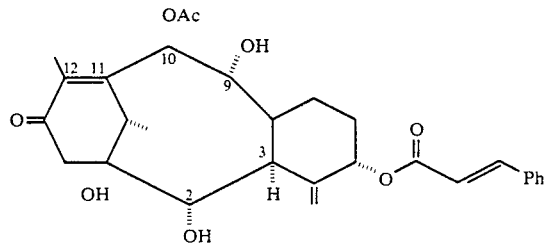

The invention concerns therefore also compound 2 as an intermediate for the synthesis of 1a. The compound 2 is also per se active as an anti-tumor agent, as hereinbelow specified.

The photochemical rearrangement of 2, having configuration E on the cinnamoyl residue, is accompanied by partial isomerization of the olefinic double bond. The material from the photocyclization consists in fact of a 5:1 mixture of the E and Z isomers. The natural product 1a has however a unitary stereoisomery, as does compound 2, having E configuration.

Re-isomerization of the portion of the Z isomer obtained from the photosynthesis to the E isomer can be achieved by refluxing the mixture from the photocyclization in tetrahydrofuran in the presence of diphenylsulfide.

The complete conversion of 2 to 1a occurs.

The photocyclization reaction of taxicins was described by K. Nakanishi (J. Chem. Soc. Chem. Commun. 1201, 1967) and it presumably occurs through a diradical intermediate in positions 3 and 11, formed by hydrogen transfer from the carbon in 3 to the carbon in 12. However the Nakanishi method relying on dioxane as a solvent gives low yields (about 50%) and, when applied to taxicins containing the cinnamoyl residues, yields stereoisomeric mixtures having high content in the Z isomer.

We have found that it is possible to obtain 1a containing at least 85% of the E isomer by carrying out the photocyclization in ethanol solution and with a low pressure mercury lamp. We also have found that it is possible to achieve the complete transformation of the mixture into the E isomer by refluxing in tetrahydrofuran in the presence of diphenylsulfide in the amount of 0.1-0.4 mol/mole of 2.

The stereochemically pure product is isolated after removal of the diphenylsulfide by silica gel chromatography, eluting with solvent mixtures such as toluene/acetone or n-hexane/ethyl acetate.

The compound 2 is extracted from needles of T. baccata L. similarly to the method described for compound 1a, for instance by extraction of the vegetable material with alcohols at room temperature, then with water immiscible solvents, silica gel chromatography and preparative HPLC.

The derivatives 1 wherein R' and/or R" represent COR'" groups can be obtained by reacting 1a (1, R'=R"=H) with a suitably activated derivative of the acid R'"COOH, e.g., the acid chloride, anhydride, or in the presence of a condensing agent, such as dicyclohexylcarbodiimide. In the first instance, the esterification is preferably carried out in a basic solvent, e.g. pyridine, with a stoichiometric amount of the acylating reagent. The reaction mixture is diluted with water and extracted with chlorinated solvent (e.g. methylene chloride or chloroform) or with an ether (e.g. ethyl ether). The organic phase is separated, washed with water and evaporated to dryness under vacuum.

The residue is then chromatographed on silica gel to give the desired ester. When dicyclohexylcarbodiimide is used, the esterification is carried out in aprotic solvent, such as dichloromethane, chloroform or dioxane.

After removal of the formed dicyclohexylurea by filtration, the reaction mixture is evaporated to dryness under vacuum and the residue is chromatographed on silica gel using as eluent solvent mixtures such as n-hexane/ethyl acetate or toluene/acetone.

It is possible to obtain a selective acylation since the hydroxy groups in position 2 and 9 of la have different reactivity.

In particular, the hydroxy in the 9-position can be acylated under mild conditions, at temperatures ranging from -50° C to the room temperature. For acylation in the 2-position, it is necessary to use stronger conditions, for instance by heating the mixture to 30-80° C, using suitable catalysts such as 4-dimethylaminopyridine, or prolonging the reaction times.

For instance compound 1b (1, R'=R''=COCH$_3$) is obtained by reacting 1a (R'=R''=H) with acetic anhydride in dry pyridine solution.

After standing overnight at room temperature, the reaction mixture is diluted with water and extracted with chloroform. The organic phase is washed with a sodium bicarbonate aqueous solution, then with water and evaporated to dryness. The residue, after silica gel column chromatography eluting with 7:3 ethyl acetate/hexane mixture, yields 1b.

The compounds of formula 1 and 2 have antimitotic activity comparable to that of known taxanes such as taxol or derivatives thereof, and in vivo, antitumor activity.

In vitro, they exhibited activity on the brain tubuline (Shelanski, Proc. Natl. Acad. Sci. USA, 70, 765, 1973) and on human cultured leucocytes. The compounds of the invention have an activity on tubuline which is twice that of the corresponding derivatives of baccatine III. The compounds can be administered orally or parenterally, alone or in combination with other therapeutic agents including anti-neoplastic agents, steroids, etc., to a mammal in need of such treatment. Parenteral routes of administration include intramuscular, intrathecal, intravenous and intraarterial. As with any drug of this type, dosage regimens must be titrated to the particular neoplasm, the condition of the patient, and the response observed but generally doses will be from about 10 to about 30 mg/m$^2$ per day for 5 days or 150 to 250 mg/m$^2$ given once every three weeks. While having a low toxicity as compared to other agents now in use, a toxic response often can be eliminated by either or both of reducing the daily dosage or administering the compound on alternative days or at longer intervals such as every three to five days. Oral dosage forms include tablets and capsules containing from 1-10 mg of drug per unit dosage. Isotonic saline solutions containing 20-100 mg/ml can be used for parenteral administration.

The following examples will clarify the main aspects of the invention.

EXAMPLE 1

Isolation of 5-O-cinnamoyl-10-acetylcyclotaxane 1a (1, R'=R''=H) from Taxus baccata leaves 500 kg of Taxus baccata leaves were extracted with 10 portions, 1500 l each of ethanol at room temperature. The collected extracts were concentrated till a 900 l volume and allowed to stand for 24 hours at room temperature. The undissolved material was separated by centrifugation and the solution was extracted with 5 portions, 300 l each, of methylene chloride. The organic phases were collected and the solvent was distilled off under reduced pressure. The obtained residue, 3.5 kg, was dissolved in a mixture containing chloroform and methanol (98:2) and was passed through a chromatography column containing 70 kg of silica gel, using the same solvent mixture as eluent.

The fractions containing pure 1a were collected, the eluent was distilled off under reduced pressure and the residue was crystallized from ethyl acetate. The compound 1a was obtained in the form of a microcrystalline white powder; m.p. 126° C., $[\alpha]_D^{20}+7.5$ (CH$_2$Cl$_2$c=0.77) UV$\lambda_{max}$ (EtOH) 279, 217, 201 nm. IR$\nu_{max}$(KBr): 3475, 1700, 1630, 1450, 1370, 1245, 1040, 990, 900, 770, 710 cm$^{-1}$. CI-MS (NH$_3$) 556 (C$_{31}$H$_{38}$O+NH$_4$)$^+$.

EXAMPLE 2

Isolation of 5-O-cinnamoyl-10-acetyltaxicine I (2)

500 kg of dried needles and small branches of T. baccata leaves were extracted with ethanol at room temperature. The residue was suspended in water and extracted with hexane and then with CHCl3 After evaporating the chloroform phase, the residue (3.5 kg) was subjected to silica gel column chromatography, using methylene chloride containing increasing amounts of methanol as eluent. The CH$_2$Cl$_2$-MeOH (98:2) fractions gave 12 g of a yellowish powder, which, after HPLC chromatography (hexane - ethyl acetate 1:1) yielded 1.5 g of 2 as a white powder, m.p. 145° C., $[\alpha]_D^{15}+185$ (CHCl$_3$, c=0.61); UV$\lambda_{max}$ EtOH nm: 280, 223, 217; IR$\nu_{max}$ KBr cm$^{-1}$: 3450, 1720, 1670, 1645, 1320, 1230, 1180, 1010, 990; CI-MS (NH$_3$) 140 eV, m/z (rel. int.): 556.

EXAMPLE 3

Preparation of 5-O-cinnamoyl-10-acetylcyclotaxane 1a (1, R''=R''=H) by photocyclization 1.05 g of 5-O-cinnamoyl-10-acetyltaxicine I (2) were dissolved in 500 ml of ethanol. The solution was put into a quartz tube and air was completely removed by bubbling nitrogen. The tube was placed into a Rayonet photochemical reactor and the solution was irradiated at 240 nm for 5 hours. The reaction mixture was then vacuum distilled to dryness and the residue was dissolved in 200 ml of tetrahydrofurane. 100 mg of diphenylsulfide were added and the mixture was refluxed for 5 hours.

The reaction mixture was then distilled to dryness and the residue was purified with a chromatography column containing 250 g of silica gel, using a mixture of n-hexane-ethyl acetate 9:1 as eluent. The chromatography was continued till complete elimination of the disulphide. Subsequent elution with n-hexaneethyl acetate 1:1 gave 1 g of 1a, which was crystallized from ethyl acetate. The obtained product had the same physicochemical characteristics as the product obtained in Example 1.

EXAMPLE 4

Preparation of 5-O-cinnamoyl-2,9,10-triacetylcyclotaxane 1b (1, R'=H R''=COCH$_3$)

200 mg of 1a were dissolved in 2 ml of anhydrous pyridine and treated with 2 ml of acetic anhydride. The reaction mixture was allowed to stand for 12 hours at room temperature, than was diluted with 15 ml of water and extracted with two portions, 5 ml each, of methylene chloride. The collected organic phases were washed with a saturated NaHCO$_3$ aqueous solution then with water and finally was evaporated to dryness. The residue was submitted to column chromatography, through 15 g of silica gel, using a n-hexane-ethyl acetate 3:7 mixture as eluent. The eluates containing 1b were vacuum distilled to dryness and gave 170 mg of white product, m.p. p.f. 90° C., CI-MS (NH$_3$) m/z 598 (C$_{31}$H$_{38}$O$_8$+NH$_4$)$^+$.

We claim:

1. A compound of the formula:

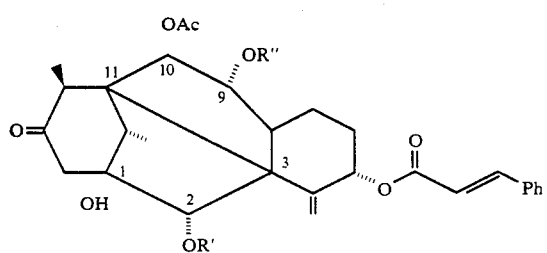

wherein each of R' and R" independently of the other is hydrogen, alkanoyl of 2 to 7 carbon atoms,

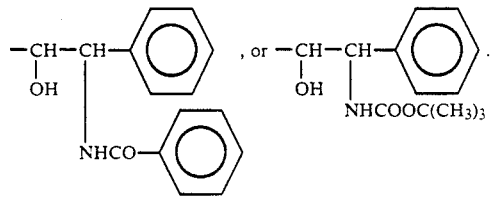

2. A compound according to claim 1 wherein each of R' and R" is hydrogen.

3. A compound according to claim 1 wherein R' is hydrogen and R" is acetyl.

4. The method of producing an antimitotic effect in a mammal in need thereof which comprises administering thereto an effective amount of a compound according to claim 1.

5. The method of producing an antimitotic effect in a mammal in need thereof which comprises administering thereto an effective amount of the compound according to claim 2.

6. The method of producing an antimitotic effect in a mammal in need thereof which comprises administering thereto an effective amount of the compound according to claim 3.

7. A pharmaceutical composition which comprises an antimitotically effective amount of the compound according to claim 1 in combination with a pharmaceutically acceptable carrier.

8. A pharmaceutical composition which comprises an antimitotically effective amount of the compound according to claim 2 in combination with a pharmaceutically acceptable carrier.

9. A pharmaceutical composition which comprises an antimitotically effective amount of the compound according to claim 3 in combination with a pharmaceutically acceptable carrier.

10. In the process for the preparation of a compound according to claim 1, the steps which comprise irradiating an ethanolic solution of a compound of the formula:

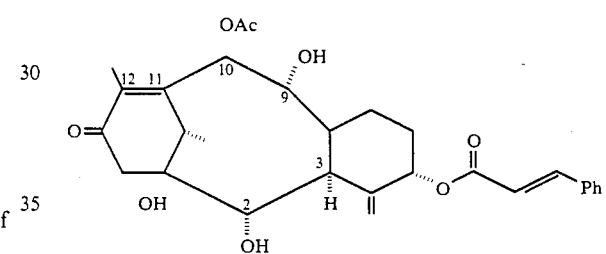

At 240 nm and treating the reaction mixture with tetrahydrofuran at reflux temperature in the presence of diphenylsulfide.

* * * * *